(12) United States Patent
Pearson et al.

(10) Patent No.: US 8,030,484 B2
(45) Date of Patent: Oct. 4, 2011

(54) SUBSTITUTED TRIAZINES AS PRION PROTEIN LIGANDS AND THEIR USE TO DETECT OR REMOVE PRIONS

(75) Inventors: James Christopher Pearson, Cambridge (GB); Helen Rosemary Tatton, Aldershot (GB); Patrick Vasconcelos Gurgel, Cary, NC (US)

(73) Assignee: Prometic Biosciences Limited, Ballasalla, Isle of Man (GB)

( * ) Notice: Subject to any disclaimer, the term of this patent is extended or adjusted under 35 U.S.C. 154(b) by 951 days.

(21) Appl. No.: 11/572,787

(22) PCT Filed: Jul. 25, 2005

(86) PCT No.: PCT/GB2005/002910
§ 371 (c)(1),
(2), (4) Date: May 14, 2007

(87) PCT Pub. No.: WO2006/010915
PCT Pub. Date: Feb. 2, 2006

(65) Prior Publication Data
US 2008/0269224 A1    Oct. 30, 2008

(30) Foreign Application Priority Data

Jul. 27, 2004 (GB) .................................. 0416699.7

(51) Int. Cl.
*C07D 251/40* (2006.01)
*C07D 251/30* (2006.01)
*C07D 251/38* (2006.01)
*C07D 251/52* (2006.01)
*C07D 251/54* (2006.01)
*A61K 31/53* (2006.01)
*A61P 25/28* (2006.01)
*A61P 43/00* (2006.01)
*G01N 33/68* (2006.01)

(52) U.S. Cl. ........ 544/194; 544/196; 544/204; 544/219; 514/241; 514/245

(58) Field of Classification Search .................. 544/194, 544/196, 204, 219; 514/241, 245
See application file for complete search history.

(56) References Cited

U.S. PATENT DOCUMENTS

| | | | |
|---|---|---|---|
| 3,850,918 A | 11/1974 | Muller et al. | |
| 4,204,060 A | 5/1980 | Hoentjen et al. | |
| 4,229,537 A | 10/1980 | Hodgins et al. | |
| 4,261,892 A | 4/1981 | Tomcufcik et al. | |
| 5,441,563 A * | 8/1995 | Sideman et al. ................. | 524/94 |
| 5,750,361 A | 5/1998 | Prusiner et al. | |
| 5,808,011 A | 9/1998 | Gawryl et al. | |
| 5,834,318 A | 11/1998 | Buettner | |
| 5,874,576 A | 2/1999 | Huber | |
| 6,479,492 B1 | 11/2002 | Konradi et al. | |
| 6,773,599 B1 | 8/2004 | Lowe et al. | |
| 2004/0186273 A1 | 9/2004 | Hammond et al. | |
| 2005/0004125 A1 | 1/2005 | Freyne et al. | |

FOREIGN PATENT DOCUMENTS

| | | |
|---|---|---|
| EP | 0398843 A1 | 11/1990 |
| GB | 814947 | 6/1959 |
| WO | 79/00609 A | 8/1979 |
| WO | 93/11155 A1 | 6/1993 |
| WO | 93/23432 A1 | 11/1993 |
| WO | 94/00513 A1 | 1/1994 |
| WO | 97/10887 A1 | 3/1997 |
| WO | 98/35236 A2 | 8/1998 |
| WO | 99/15651 A1 | 4/1999 |
| WO | 00/02575 A1 | 1/2000 |
| WO | 00/67900 A | 11/2000 |
| WO | 00/67900 A1 | 11/2000 |
| WO | 0177687 A2 | 10/2001 |
| WO | 02/098878 A1 | 12/2002 |
| WO | 03/037891 A1 | 5/2003 |
| WO | 03/050237 A2 | 6/2003 |
| WO | 2004/035199 A | 4/2004 |
| WO | 2004/052870 A1 | 6/2004 |
| WO | 01/77687 A2 | 10/2004 |
| WO | 2006/131550 A1 | 12/2006 |

OTHER PUBLICATIONS

Gilch et al., Expert Opin. Biol. Ther., 2008 8(7):923-40.* Rajnani et al., Journal of the Institution of Chemists(India), 50(5), 213-214, 1978; CA 91:74571,1979. CAPLUS Abstract provided.*
Moriga, H. JP 49039721(Oct. 24, 1974); CA 82:171089, 1975. CAPLUS Abstract provided.*
Renou et al., "The Design, Synthesis and Evaluation of Affinity Ligands for Prion Proteins," J. Mol. Recognit. 17 (3):248-261 (2004).
Stankova et al., "Library Generation Through Successive Substitution of Trichlorotriazine," Mol. Divers. 2(1-2):75-80 (1996).
Scharn et al., "Spatially Addressed Synthesis of Amino- and Amino-Oxy-Substituted 1,3.5-Triazine Arrays on Polymeric Membranes," J. Comb. Chem. 2(4):361-369 (2000).
Palanisamy et al., "Design, Synthesis and Characterisation of Affinity Ligands for Glycoproteins," J. Mol. Recognit. 12(1):57-66 (1999).
Filippusson et al., "Design, Synthesis and Evaluation of Biomimetic Affinity Ligands for Elastases," J. Mol. Recognit. 13(6):370-381 (2000).

(Continued)

*Primary Examiner* — Venkataraman Balasubramanian
(74) *Attorney, Agent, or Firm* — LeClairRyan

(57) ABSTRACT

Compounds of formula (I) wherein $R^1$ and $R^2$ are the same or different and are each optionally substituted alkyl, optionally substituted cycloalkyl, optionally substituted aryl or optionally substituted heteroaryl groups; $R^3$ is hydrogen or an aryl group substituent or $R^3$ is a solid support optionally attached via a spacer; Z represents an oxygen atom, a sulphur atom or $NR^4$; Y represents an oxygen atom, a sulphur atom or $NR^5$; in which $R^4$ and $R^5$, which may be the same or different, represent hydrogen, optionally substituted alkyl containing 1 to 6 carbon atoms, optionally substituted phenyl, optionally substituted benzyl or optionally substituted β-phenylethyl; and one of $X^1$ and $X^2$ represents a nitrogen atom and the other of $X^1$ and $X^2$ represents a nitrogen atom or $CR^6$, in which $R^6$ represents hydrogen or an aryl group substituent; are useful for the affinity binding of a prion protein.

(I)

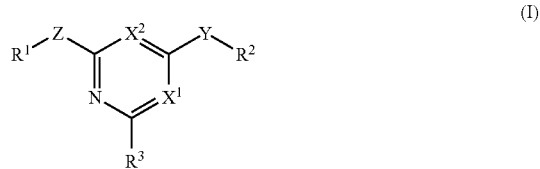

3 Claims, No Drawings

OTHER PUBLICATIONS

Chemical Abstract Accession No. 131:271860 (Hedayatullah et al., "Synthesis of Reactive s-triazines Bearing a Cage System Derived from Adamantane as Precursors for Hexamethylmelamine Analogues," Heterocycles 51 (8):1891-1896 (1999)).

Chemical Abstract Accession No. 1990:631333 (Kreutzberger et al, "2-Chloro-4,4-diamino-1,3,5-triazines," Chemiker-Zeitung 114(6): 204-208 (1990)).

Chemical Abstract Accession No. 1994:435553 (Paleos et al, "Mesomorphic Character of Some Long-Chain 2,4,6-trichloro-1,3,5-triazine Derivatives Susceptible to Facile Functionalization," Molecular Crystals and Liquid Crystals 242: 277-283 (1994)).

Chemical Abstract Accession No. 87:152135 (Tadid et al, "Thermal Dealkylation of 2,4-bis(alkylamino)-6-chloro-s-triazines," Chemistry Society 11: 1257-1259 (1977)).

Acosta et al, "Dendritic Surfactants Show Evidence for Frustrated Intercalation: A New Organoclay Morphology," Chemistry of Materials 15(15): 2903-2909 (2003).

Graubaum et al, "Polyazacalix[5]arene—Synthese und NMR-Untersuchungen," Journal für Praktische Chemie 339 (1): 266-271 (1997) (Abstract in English, p. 266).

Kreutzberger et al, "Antidiabetische wirkstoffe und verzweigtkettig substituierte chlor-dihexylamino-1,3,5-triazine," Journal of Heterocyclic Chemistry 22(5): 1441-1444 (1985) (Abstract in English, p. 271).

Kreutzberger et al, "Herbizide, V1 [1], Kernfluorierte 2,4-Dianilino-6-(Diehexylamino)-1,3,5-Triazine," Journal of Fluorine Chemistry 30: 329-341 (1985) (Abstract in English, p. 341).

Omokawa et al, "Reverse Chiral Discrimination Relationships between the Inhibitory Activity of 1,3,5-Triazines on Photosystem II and Light-independent Root Growth," Pesticide Biochemistry and Physiology 50(10): 129-137 (1994).

Schnabel et al, "The Synthesis of Substituted Melams," Organic Chemistry 27(7): 2514-2519 (1962).

Thurston et al, "Cyanuric Chloride Derivatives Aminochloro-s-triazines," JACS 73(7): 2981-2983 (1951).

Caughey et al., "Binding of Protease-Sensitive Form of Prion Protein PrP to Sulfated Glycosaminoglycan and Congo Red.," J. Virol. 68:2135-2141 (1994).

Fischer et al., "Binding of Disease-Associated Prion Protein to Plasminogen," Nature 408:479-483 (2000).

Ingrosso et al., "Congo Red Prolongs the Incubation Period in Scrapie-Infected Hamster," J. Virol. 69:506-508 (1995).

Kascsak et al., "Immunodiagnosis of Prion Disease," Immunol. Investigation 26:259-268 (1997).

Priola et al., "Porphyrin and Phthalocyanine Antiscrapie Compounds," Science 287:1503-1506 (2000).

Soto et al., "Reversion of Prion Protein Conformational Changes in Synthetic Beta-Sheet Breaker Peptides," Lancet 355:192-197 (2000).

Stockel et al., "Prion Protein Selectively Binds Copper (II) Ions," Biochemistry 37:7185-7193 (1998).

Tagliavani et al., "Effectiveness of Anthracycline Against Experimental Prion Diseases in Syrian Hamsters," Science 276:1119-1122 (1997).

* cited by examiner

SUBSTITUTED TRIAZINES AS PRION PROTEIN LIGANDS AND THEIR USE TO DETECT OR REMOVE PRIONS

This application is a national stage application of PCT/GB2005/002910 under 35 U.S.C. 371 and claims the priority benefit of British Patent Application GB 0416699.7, filed Jul. 27, 2004.

FIELD OF THE INVENTION

This invention relates to the field of protein-ligand interactions and more particularly to compounds that bind to prion proteins ("prion protein ligands") and methods of using the compounds to detect or remove prions from biological samples.

BACKGROUND OF THE INVENTION

Native or cellular prion protein "PrPc" is widely distributed throughout the mammalia and has a particularly well-conserved amino acid sequence and protein structure. Infectious prions are thought to be composed of a modified form of the normal cellular (PrPc) prion protein and are called "PrPsc". Prions have some properties in common with other infectious pathogens, but do not appear to contain nucleic acid. Instead, it is proposed that a post-translational conformational change is involved in the conversion of non-infectious PrPc into infectious PrPsc during which α-helices are transformed into α-sheets. PrPc contains three α-helices and has little β-sheet structure; in contrast, PrPsc is rich in β-sheet. The conversion of PrPc to PrPsc is believed to lead to the development of transmissible spongiform encephalopathies (TSEs) during which PrPsc accumulates in the central nervous system (CNS) and is accompanied by neuropathologic changes and neurological dysfunction. PrPsc, often referred to as the "scrapie" form of the prion protein, is considered necessary and possibly sufficient for the transmission and pathogenesis of these transmissible neurodegenerative diseases of animals and humans.

Specific examples of TSEs include scrapie, which affects sheep and goats; bovine spongiform encephalopathy (BSE), which affects cattle; transmissible mink encephalopathy; feline spongiform encephalopathy; and chronic wasting disease (CWD) of mule deer, white-tailed deer, black-tailed deer and elk. In humans, TSE diseases may present themselves as kuru, Creutzfeldt-Jakob disease (CJD), Gerstmann-Straussler-Scheinker Syndrome (GSS), fatal insomnia and variant Creutzfeldt-Jakob disease (vCJD). vCJD recently emerged in humans as a result of the BSE epidemic in Britain and is most probably caused by the consumption of food products derived from cattle infected with BSE or "mad cow disease". An unknown number of people in the UK ingested food potentially contaminated with nervous tissue from BSE-infected cattle during the mid 1980s to early 1990s. Because the incubation period for the orally contracted disease may be more than 20 years in humans, the true incidence of vCJD may not become apparent for many years. To date, over 150 people are known to have contracted the disease, primarily in the UK; however, cases have also been reported in Canada, France, Hong Kong, Ireland, Italy, and the US. The export of contaminated bovine feed products from the UK worldwide indicates a possible global presence of BSE and hence the probability of vCJD. Consistent with these observations is the detection of BSE in most European countries, Canada, USA, Japan and Israel. Consequently, the ability to detect and remove infectious prion protein from a variety of materials including food products is of profound importance.

Historically, the diagnosis of TSEs was based on the occurrence of clinical signs of the disease and could be confirmed only by post-mortem histological examination of brain tissue. A characteristic of all TSEs is the lack of a measurable host immune response to the agent. Thus, no antibodies are produced and no conventional serologic test can be used to identify infected animals. Recently, identification of abnormal prion protein in the brain has improved the ability to make a disease diagnosis.

In addition to ingestion of infected products of bovine origin, blood transfusion and organ transplantation represent another potential mode of transmission of vCJD among humans. There have been two suspected cases of vCJD transmission by blood transfusion in the U.K. The infectivity of vCJD in humans by blood transfusion is currently unknown but there is increasing concern this may be a more effective means of vCJD transmission compared to ingestion. This is consistent with data from experimental animal models including transmission from sheep. Unlike other human TSEs, PrPsc is present in the lymphoreticular system of vCJD patients, thereby increasing the probability of the infectious agent being in blood and its transmission through blood transfusion. Other factors elevating concern about the risk of transmission by transfusion include the unknown, but presumably high, numbers of people exposed to BSE and the lack of a preclinical diagnostic test for vCJD. Moreover, the virulence of vCJD appears to be enhanced following species adaptation in primates and mice, suggesting that human-to-human transmission may be more efficient than cow-to-human. Thus, there is an urgent need for methods to prevent the transmission of vCJD by blood transfusion. Such measures may include early identification of infected donors and the removal and inactivation of TSE agents in animal-derived food and health products intended for animal or human consumption or applications, human and bovine blood-derived products, and organ transplants. Unfortunately, PrPsc is remarkably resistant to chemical and physical methods of inactivation, and a selective method of inactivation is elusive.

Prion removal through the specific interaction with ligands appears more promising. A number of ligands have already been identified that bind to prion protein. Combinatorial peptide libraries have been screened for ligands that bind to the octapeptide repeat sequence (PHGGGWGQ, SEQ ID NO: 1) found in all known mammalian prion proteins and a series of ligands were discovered, as described in WO 01/77686. Other materials include a variety of polymers, eg amino polymethacrylate from TosoBioSep, ion exchange resins generally (see U.S. Pat. No. 5,808,011 to Gawryl et al), ligands that interact with amyloid plaque eg Congo Red (Ingrosso et al, J. Virology 69:506-508 (1995)), 4-iodo, 4-deoxy doxorubicin (Tagliavini et al, Science 276:1119-1122 (1997)), amphotericin B, porphyrins and phthalocyanines (Priola et al, Science 287:1503-1506 (2000)), metals (Stockel et al, Biochemistry, 37, 7185-7193 (1998)), peptides that interact with PrP to form complexes (see U.S. Pat. No. 5,750,361 to Prusiner et al and Soto et al, Lancet, 355:192-197 (2000)), heparin and other polysulphated polyanions (Caughey et al, Binding of the Protease-sensitive form of prion protein PrP to Sulphated Glycosaminoglycan and Congo Red, J. Virology 68:2135-2141 (1994)), antibodies (Kascsak et al, Immunological Invest. 26:259-268 (1997)), and other proteins, eg plasminogen (Fischer et al, Nature 408:479-483 (2000)). Currently, no ligand has been fully characterized or found to be able to bind to prion from a wide variety of media, although some may be useful in specific circumstances (see U.S. Pat. No. 5,808,011 to Gawryl et al).

To date, human TSE diseases are 100% fatal. Unfortunately, even though a number of compounds including amphotericins, sulphated polyanions, Congo Red dye and anthracycline antibiotics have been reported as prospective therapeutic agents, all have demonstrated only modest potential to impede prion propagation, and none have been shown to have any effect on the removal of pre-existing prions from an Thus, in a further aspect of the invention, there is provided a method of treating, or retarding the development of, a prion-associated pathology in a human or animal subject, which method comprises administering to the subject a therapeutically effective amount of a compound of formula (I) that is not bound to a solid support.

Similarly, the invention further provides the use of a compound of formula (I) that is not bound to a solid support in the manufacture of a medicament for the treatment of a prion-associated pathology.

Other features and advantages of the invention will be apparent from the following detailed description and preferred embodiments.

DETAILED DESCRIPTION OF THE INVENTION

Definitions

The terms "a," "an" and "the" as used herein are defined to mean "one or more" and include the plural unless the context is inappropriate.

The term "3F4" refers to the monoclonal antibody specific to native forms of PrPc, but not native PrPsc or PrPres. The antibody has specificity for denatured forms of hamster and human PrPc, PrPsc and PrPres.

The term "alkenyl" refers to an aliphatic hydrocarbon group containing a carbon-carbon double bond and which may be straight or branched. Preferred alkenyl groups have 2 to 12 carbon atoms in the chain, and more preferably 2 to 6 carbon atoms in the chain, eg propenyl, n-butenyl, iso-butenyl, 3-methylbut-2-enyl, n-pentenyl and heptenyl. The terms "cycloalkenyl" and "heterocycloalkenyl" are analogous.

The term "alkoxy" refers to an alkyl-O— group in which the alkyl is as described herein. Examples include methoxy, ethoxy, propoxy, isopropoxy, butoxy and pentoxy.

The term "alkyl" as used herein, alone or in combination, refers to a straight or branched, saturated hydrocarbon having 1 to 15 carbon atoms. Lower alkyl groups with 1 to 6 carbons are preferred, eg methyl, ethyl, n-propyl, isopropyl, n-butyl, sec-butyl, isobutyl, tert-butyl, n-pentyl, 2-methylbutyl, 3-methylbutyl, n-hexyl, 4-methylpentyl, neopentyl and 2,2-dimethylpropyl. Where an alkyl group is described as "optionally substituted" then that group may be substituted by one or more substituents, particularly by one or more "alkyl group substituents" as defined herein.

The term "alkyl group substituent" refers, unless otherwise defined, to hydroxyl, amino, alkyl, halogen, hydroxyalkyl, amide, acyl, acylamino, alkoxy, alkoxycarbonyl, alkylenedioxy, alkylsulfinyl, alkylsulfonyl, alkylthio, aroyl, aroylamino, aryl, arylalkoxy, arylalkoxycarbonyl, arylalkylthio, aryloxy, aryloxycarbonyl, arylsulfinyl, arylsulfonyl, arylthio, carboxy (or an acid bioisostere), cyano, heteroaroyl, heteroaryl, heteroarylalkyloxy, heteroaroylamino, heteroaryloxy, nitro or trifluoromethyl.

The term "aroyl" refers to an aryl-CO— group in which the aryl group is as described herein, eg benzoyl, and 1- and 2-naphthoyl.

The term "aryl" as a group or part of a group refers to:
a) an optionally substituted monocyclic or multicyclic aromatic carbocyclic moiety of 6 to 18 carbon atoms, such as phenyl, naphthalene, aceanthrylene, acenaphthylene, acephenanthrylene, azulene, chrysene, indacene, indene, fluorine, phenalene, and phenanthrene; or
b) an optionally substituted partially saturated multicyclic aromatic carbocyclic moiety in which an aryl and cycloalkyl, cycloalkenyl, heterocycloalkyl or heterocycloalkenyl are fused together to form a cyclic structure, such as a indolinyl, tetrahydronaphthyl, indenyl or indanyl ring.

Preferred aryl groups are optionally substituted phenyl groups.

Where an aryl group is described as "optionally substituted" then that group may be substituted by one or more substituents, particularly by one or more one or more "aryl group substituents" as defined herein.

An "aryl group substituent" refers, unless otherwise defined, to a hydroxyl, amino, alkyl, halogen, hydroxyalkyl, amide, acyl, acylamino, alkoxy, alkoxycarbonyl, alkylenedioxy, alkylsulfinyl, alkylsulfonyl, alkylthio, aroyl, aroylamino, aryl, arylalkoxy, arylalkoxycarbonyl, arylalkylthio, aryloxy, aryloxycarbonyl, arylsulfinyl, arylsulfonyl, arylthio, carboxy (or an acid bioisostere), cyano, heteroaroyl, heteroaryl, heteroarylalkyloxy, heteroaroylamino, heteroaryloxy, nitro, oxo or trifluoromethyl.

As used herein, the term "blood-derived compositions" is meant to include whole blood, red blood cell concentrate, plasma, serum, platelet-rich and platelet-poor fractions, platelet concentrates, white blood cells, blood plasma precipitates, blood plasma fractionation precipitates and supernatants, immunoglobulin preparations including IgA, IgE, IgG and IgM, purified coagulation factor concentrates, fibrinogen concentrate, or various other compositions which are derived from humans or animals. It also includes purified blood-derived proteins prepared by any of various methods common in the art including ion exchange, affinity, gel permeation, and/or hydrophobic chromatography or by differential precipitation.

The term "combinatorial library" refers to a collection of chemicals that have been synthesized by solid-phase combinatorial chemistry techniques. This definition encompasses using a split-couple-recombine method that generates millions of random compounds or may be designed to include defined structures. The building blocks may be triazine scaffolds, and the like.

The term "cycloalkyl" refers to a saturated monocyclic, bicyclic or polycyclic ring system of 3 to 12 carbon atoms, with or without a side-chain, and optionally interrupted by —(C=O)—. Preferred cycloalkyl groups are monocycloalkanes, eg cyclopropyl, cyclopentyl, cyclohexyl, cycloheptyl; bicycloalkanes that are connected at one carbon, eg sprionoanane; and saturated bridged ring systems including bicycloalkanes that are connected at two carbons, eg norbornane, bicyclo[4.3.2]undecane, bicycle[4.1.0]heptane and decalin, and polycyclic bridged systems, eg adamantine. More preferably, the cycloalkyl group is a monocycloalkane or bridged ring system. Most preferably the cycloalkyl group is cyclohexyl, norbornane or adamantane.

Where a cycloalkyl group is described as "optionally substituted" then that group may be substituted by one or more substituents, particularly by one or more one or more "alkyl group substituents" as defined herein.

The term "halogen" means fluorine, chlorine, bromine or iodine.

The term "heteroaryl" as a group or part of a group refers to:
a) an optionally substituted monocyclic aryl in which one or more of the ring members is/are element(s) other than carbon, for example N, O or S, and preferred examples are monocyclic or bicyclic, eg benzimidazoyl, benzthiazoyl, furyl, imidazoyl, indolyl, indolizinyl, isoxazoyl, isoquinolyl, isothiazoyl, oxadiazoyl, pyranyl, pyrazinyl, pyridazinyl, pyrazoyl, pyridyl, pyrimidinyl, pyrrolyl, quinazolinyl, quinolyl, 1,3,4-thiadiazolyl, thiazolyl, thienyl and triazolyl groups, optionally substituted with one or more aryl group substituents as defined herein, unless otherwise defined; or b) an optionally substituted partially saturated multicyclic heterocarbocyclic moiety in which a heteroaryl and a cycloalkyl, cycloalkenyl, heterocycloalkyl or heterocyloalkenyl group are fused together to form a cyclic structure (examples of such groups include pyrindanyl groups, optionally susbstituted by one or more aryl group substituents as defined herein, except where defined otherwise).

Where a heteroaryl group is described as "optionally substituted" then that group may be substituted by one or more substituents, particularly by one or more one or more "aryl group substituents" as defined herein.

The term "heterocycloalkyl" refers to a cycloalkyl group with at least one ring carbon atom replaced by a heteroatom or heteroatom-containing group, eg O, S, N or $NR^7$, where $R^7$ is hydrogen or alkyl. Preferred heterocycloalkyl groups contain one or more N atoms, eg imidazolidine, piperidine, morpholine, piperazine, pyrrolidinone, pyrazolidine and quinuclidine. More preferred examples are heteromonocycloalkanes with one or more N atoms, eg piperidine and piperazine. Where a heterocycloalkyl group is described as "optionally substituted" then that group may be substituted by one or more substituents, particularly by one or more one or more "alkyl group substituents" as defined herein.

The term "hydrophobic group" refers to a lipophilic group which is usually electrically neutral and non-polar. Hydrophobic groups prefer neutral and non-polar solvents or molecular environments, as opposed to aqueous solvents or environments. A hydrophobic group will, therefore, have an affinity for other hydrophobic groups in a normal physiological environment. Examples of hydrophobic groups usually include alkyl and cycloalkyl groups, preferably unsubstituted, and aryl groups.

The compounds described in the invention will generally be used at a pH that is the same as, or close to, physiological pH. The hydrophobic character of the compounds, or of particular moieties within those compounds, will be determined by whether the moiety concerned is charged at such a pH. For example 1-(2-aminoethyl)piperidine is a hydrophobic group when, at physiological pH, the nitrogen is uncharged.

The term "ligand" refers to a molecule to which a protein, peptide or polypeptide binds. The ligands of the present invention are substituted heteroaromatic compounds such as triazines.

The term "PrPc" refers to the native prion protein molecule which is naturally and widely expressed within the body of the mammalia. Its structure is highly conserved and is not associated with a disease state.

The term "PrPsc" refers to the conformationally altered form of the PrPc molecule that is that is thought to be infectious and is associated with TSE/prion diseases, including vCJD, CJD, kuru, fatal insomnia, GSS, scrapie, BSE, CWD, and other rare TSEs of captive and experimental animals. It has the same amino acid sequence as normal, cellular PrPc, but some of the α-helix is converted to β-sheet and is associated with a disease state.

The term "PrPres" refers to the proteinase resistant derivatives of the PrPsc protein of 27-30 kDa that remain following partial digestion of PrPsc with PK.

The term "PrP" refers to prion protein in general.

The term "spacer" refers to an optional moiety that connects the affinity ligand to a support matrix. One preferred class of spacer is represented by the general formula (II):

$$\text{-T-[L-V-]}_a\text{-} \quad \text{(II)}$$

wherein

T represents O, S or $NR^7$;

V represents an —O—, —S—, —COO—, —CONH— or —NHCO—, —PO$_3$H—, —NH-arylene-SO$_2$—CH$_2$CH$_2$— or —NR$^7$—;

L represents an optionally substituted hydrocarbon linkage containing 2 to 20 carbon atoms; and a is 0 or 1.

The term "support matrix" refers to any compound or material, whether particulate or non-particulate, soluble or insoluble, porous or non-porous, which may be used to form an affinity ligand-matrix conjugate according to the invention and which provides a convenient means of separating the affinity ligands from solutes in a solution. The support matrix may therefore take the form of a column, beads, small particles, a membrane or a mesh, for example.

Examples of support matrices include soluble support matrices such as naturally occurring polymers, eg a polypeptide or a protein such as cross-linked albumin or a polysaccharide such as agarose, alginate, carrageenan, chitin, cellulose, dextran or starch; synthetic polymers such as polyacrylamide, polystyrene, polyacrolein, polyvinyl alcohol, polymethylacrylate, perfluorocarbon; inorganic compounds such as silica, glass, kieselguhr, alumina, iron oxide or other metal oxides, or copolymers consisting of any combination of two or more naturally occurring polymers, synthetic polymers or inorganic compounds.

Also included within the definition of support matrices are soluble support matrices comprising polymers such as dextran, polyethylene glycol, polyvinyl alcohol or hydrolysed starch which provide affinity-ligand matrix conjugates for use in liquid partitioning; or solid support matrices comprising compounds such as perfluorodecalin which provide affinity-ligand matrix conjugates for use in the formation of affinity emulsions.

Further included within the definition of support matrices are support matrices such as agarose, cellulose, dextran, starch, alginate, carrageenan, synthetic polymers, silica, glass and metal oxides which have been, or are, modified by treatment with an activating agent prior to, or during, attachment of the ligand.

Support matrices are preferably optionally activated agarose, silica, cellulose, glass, methacrylate, hydroxyethylmethacrylate, polyacrylamide, styrenedivinylbenzene, Hyper D or perfluorocarbons. Most preferably the support matrix is a methacrylate material, of the type sold under the trade name Toyopearl (available from Tosoh Bioscience LLC, 156 Keystone Drive, Montgomeryville, Pa. 18936, USA).

WO 97/10887 describes methods of attaching affinity ligands to support matrices, eg the use of activating methods, and methods of attaching the affinity ligand to a matrix via a spacer, eg by condensation reactions, to form affinity ligand-matrix conjugates.

Compounds of formula (I) are preferred in which both $X^1$ and $X^2$ represent nitrogen atoms.

Compounds of formula (I) are preferred in which both Z and Y represent $NR^4$, in particular where $R^4$ is hydrogen.

It is preferred that at least one of $R^1$ and $R^2$ represents an optionally substituted alkyl group.

In a first group of particularly preferred compounds of general formula (I), referred to as compounds of formula (Ia):

R³ is as defined above;
X¹ and X² are as defined above;
Y is as defined above;
Z is as defined above;
R¹ represents a group —(CH₂)$_m$-Q¹, wherein m is from 0 to 7, and Q¹ represents —CR¹¹R¹²R¹³ or —NR¹¹R¹², in which R¹¹, R¹² and R¹³ independently represent hydrogen, alkyl, cycloalkyl or heterocycloalkyl, or two of R¹¹, R¹² and R¹³, together with the carbon or nitrogen atom to which they are attached, form an optionally substituted cycloalkyl or optionally substituted heterocycloalkyl group; and
R² represents a group —(CH₂)$_n$-Q², wherein n is from 0 to 7, and Q² represents —CR²¹R²²R²³ or —NR²¹R²² in which R²¹R²² and R²³ independently represent hydrogen, alkyl, cycloalkyl or heterocycloalkyl, or two of R¹¹, R¹² and R¹³, together with the carbon or nitrogen atom to which they are attached, form an optionally substituted cycloalkyl or optionally substituted heterocycloalkyl group.

In compounds of formula (Ia):
a) X¹ and X² are preferably both nitrogen;
b) both Z and Y preferably represent NR⁴, in particular where R⁴ is hydrogen;
c) m is preferably from 0 to 4, more preferably from 0 to 3, and most preferably from 1 to 3;
d) Q¹ is preferably —NR¹¹R¹²; and R¹¹ and R¹² preferably form, together with the nitrogen atom to which they are attached, a heterocycloalkyl group;
e) n is preferably from 0 to 4, more preferably from 0 to 2, and most preferably is 0; and
f) R²¹ and R²² preferably form, together with the carbon atom or nitrogen atom to which they are attached, a cycloalkyl or heterocycloalkyl group.

Particularly preferred groups that Q² may represent include hydrophobic cycloalkyl and heterocycloalkyl groups, especially with ring systems that comprise at least six atoms. Examples of such groups include cyclohexyl, piperidyl, particularly 1-piperidyl, and bridged carbocyclic ring systems, eg norbornyl. Such groups are preferably unsubstituted, particularly not substituted with any polar substituents.

Particular groups that Q¹ may represent include heterocycloalkyl groups, especially piperidyl, particularly 1-piperidyl, and piperazinyl, particularly 1-piperazinyl.

In a second group of particularly preferred compounds of general formula (I), referred to as compounds of formula (Ib):
R³ is as defined above;
X¹ and X² are as defined above;
Y is as defined above;
Z is as defined above;
R¹ represents an alkylene chain —(CH₂)$_p$—CH₃, wherein p is from 0 to 6, substituted by one or more carboxyl groups and optionally substituted by one or more further alkyl group substituents; and
R² represents a group —(CH₂)$_q$—Ar, wherein q is from 0 to 7, and Ar represents an optionally substituted aryl group.

In compounds of formula (Ib):
a) X¹ and X² are preferably both nitrogen;
b) both Z and Y preferably represent NR⁴, in particular where R⁴ is hydrogen;
c) p is preferably from 0 to 4, more preferably from 0 to 3;
d) R¹ is preferably substituted with one or two carboxyl groups, at least one of those carboxyl groups being carried by the terminal carbon atom of the alkylene chain —(CH₂)$_p$—CH₃;
e) q is preferably from 0 to 4, more preferably from 0 to 3, and most preferably is 1 or 2; and
f) Ar is preferably a monocyclic carbocyclic or heterocyclic aromatic group, optionally substituted by one or more substituents selected from the group consisting of phenyl, phenoxy, tolyl, chlorobenzyl, methoxybenzyl, fluorobenzyl, pyridyl and indoyl. Ar is more preferably phenyl, phenoxy or pyridyl.

Particularly preferred groups that R¹ may represent are carboxymethyl, 4-carboxybutyl and 1-(1,3-dicarboxy)propyl.

Particularly preferred groups that Ar may represent include phenyl, 4-hydroxyphenyl and pyridyl, particularly 2-pyridyl.

Compounds of formulae (Ia) and (Ib) are novel, and represent further aspects of the present invention.

One set of specific compounds of formula (I) that have been found to be useful in the invention is compounds of formula (Ia) in which:
R³ is as defined above;
X¹ and X² are both N;
Y and Z both represent NH;
m represents 2;
Q¹ represents piperidyl or piperazinyl;
n represents 0 or 2; and
Q² represents 1-piperidyl or adamantyl.

Another set of specific compounds of formula (I) that have been found to be useful in the invention is compounds of formula (Ib) in which:
R³ is as defined above;
X¹ and X² are both N;
Y and Z both represent NH;
R¹ represents carboxymethyl, 4-carboxybutyl and 1-(1,3-dicarboxy)propyl;
q represents 2; and
Ar represents phenyl, 2-pyridyl or 4-hydroxyphenyl.

DESCRIPTION OF PREFERRED EMBODIMENTS

Preferred embodiments of the present invention, will now be described, by way of illustration only, with reference to the following methodologies and Examples.

Synthesis of Ligands

Methods by which compounds of formula (I) may be prepared will in general be evident to those skilled in the art. Reference may be made, for instance, to the methods of synthesis disclosed in WO97/10887.

One method by which compounds of formula (I) may be prepared involves reaction of a compound of general formula (II)

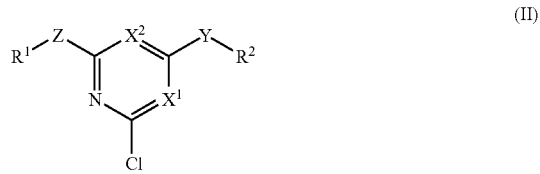

in which R¹, Z, R², Y, X¹ and X² are as defined above in relation to formula (I), with an amine-containing support matrix.

Another method by which compounds of formula (I) may be prepared involves reaction of a compound of formula (III)

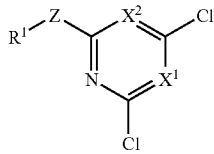
(III)

in which $R^1$, Z, $X^1$ and $X^2$ are as defined above in relation to formula (I), with an amine-containing support matrix to form a compound of formula (IV)

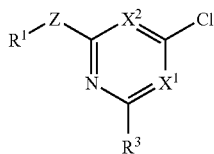
(IV)

in which $R^1$, Z, $X^1$ and $X^2$ are as defined above in relation to formula (I) and $R^3$ represents the support matrix optionally attached via a spacer, followed by reaction of the compound of formula (IV) with a compound of formula H—Y—$R^2$.

In a further general preparative method, a compound of formula (V)

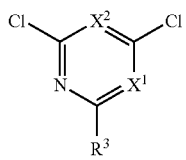
(V)

in which $X^1$ and $X^2$ are as defined above in relation to formula (I) and $R^3$ represents a support matrix optionally attached via a spacer, is reacted sequentially with compounds of formula H—Z—$R^1$ and H—Y—$R^2$.

Ligand Identification

Ligands can be identified as follows. Mimetic libraries are synthesized and screened for the ability to bind to prion analytes. Prion analyte is passed through the column and bound analyte is detected using conventional methods such as by a labelled antibody specific for prion protein. Beads to which the analyte has bound are identified as being suitable ligands.

Use of Ligands to Remove Prions

Ligands that bind prions or fragments of prions are useful for a variety of analytical, preparative, and diagnostic applications. Prion-binding ligands may be immobilized on a support such as a bead or membrane, and used to bind and remove prion from a sample. The solid phase to which the ligands are bound is allowed to contact the sample, such as a biological fluid, under conditions sufficient to cause formation of a prion-ligand composite, and prion protein in the sample binds to the ligand. The solid phase is then separated from the sample, thereby removing the prion protein bound to the ligand, which is attached to the solid phase, from the sample. For example, resins and membranes for removal of contaminants are well known in the art such as those described in U.S. Pat. No. 5,834,318 to Baumbach et al and WO 01/77687.

Examples of biological samples include, but are not limited to, blood, blood-derived compositions and serum. Additional biological samples include cerebrospinal fluid, urine, saliva, milk, ductal fluid, tears or semen. Other samples may contain collagen, brain and gland extracts.

Many methods for immobilizing molecules to a variety of solid surfaces are known in the art. For instance, the solid surface may be a membrane (eg nitrocellulose), a microtiter dish (eg PVC, polypropylene, or polystyrene), a test tube (glass or plastic), a dipstick (eg glass, PVC, polypropylene, polystyrene, latex, and the like), a microcentrifuge tube, or a glass, silica, plastic, metallic or polymer bead. The desired component may be covalently bound, or noncovalently attached through nonspecific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, polyacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which may be employed, include paper, glasses, ceramics, metals, metalloids, semiconductive materials, cements or the like. In addition, substances that form gels, such as proteins (eg gelatins), lipopolysaccharides, silicates, agarose and polyacrylamides can be used. Polymers which form several aqueous phases, such as dextrans, polyalkylene glycols or surfactants, such as phospholipids, long chain (12-24 carbon atoms) alkyl ammonium salts and the like are also suitable. Where the solid surface is porous, various pore sizes may be employed depending upon the nature of the system. In addition, the peptide may be incorporated during polymerization of the solid surface.

In preparing the surface, a plurality of different materials may be employed, eg as laminates, to obtain various properties. For example, protein coatings, such as gelatin can be used to avoid non specific binding, simplify covalent conjugation, and enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature.

Prion proteins may also be separated from other proteins in a sample by using affinity chromatography. Ligands according to the invention can be attached to a solid support, such as a resin or membrane, and used to bind and remove the prion from solution. In this instance, the ligand may be coupled to a solid support, eg an inert support such as a membrane or a resin, and the prion protein binds to the immobilized agent. The immobilized agent/prion may be detected by means of antibodies. If desired, one or more of the sequences obtained from the initial screening may be immobilized on a resin, such a polymethacrylate or agarose. Other types of resin that may be used include, eg sepharose, cross-linked agarose, composite cross-linked polysaccharides, celite, PVDF, acrylate, polystyrene and cellulose. Membranes such as, for example, nylon and cellulose may also be used. The resin may be a polymethacrylate resin.

Use of Ligands to Detect Prions

The ligands described herein are also useful in a method of detecting the presence of or quantifying a prion protein in a biological sample. A biological sample such as, but not limited to, those listed above is contacted with a ligand under conditions sufficient to cause formation of a complex between the prion protein and the ligand. The complex is then detected by conventional methods, thereby detecting the presence of the prion in the biological sample.

The complex is detected by labelling the ligand, combining the labelled ligand with the sample, and detecting labelled ligand-prion complex. The ligand is labelled during ligand production, such as during peptide synthesis, or a label is conjugated to the ligand by joining it to the ligand, either covalently or non-covalently. Alternatively, a binding molecule specific for the ligand, such as an antibody, is labelled and the complex is detected indirectly. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like.

Detection may proceed by any known method, such as immunoblotting, western analysis, gel-mobility shift assays, fluorescent in situ hybridization analysis (FISH), tracking of radioactive or bioluminescent markers, nuclear magnetic resonance, electron paramagnetic resonance, stopped-flow spectroscopy, column chromatography, capillary electrophoresis, or other methods which track a molecule based upon an alteration in size and/or charge. The particular label or detectable group used in the assay is not a critical aspect of the invention. The detectable group can be any material having a detectable physical or chemical property. Such detectable labels have been well-developed and, in general, any label useful in such methods can be applied to the present method. Thus, a label is any composition detectable by spectroscopic, photochemical, biochemical, immunochemical, electrical, optical or chemical means. Useful labels in the present invention include fluorescent dyes (eg fluorescein isothiocyanate, Texas, red, rhodamine, and the like), radiolabels (eg $^3H$, $^{125}I$, $^{35}S$, $^{14}C$, or $^{32}P$), enzymes (eg LacZ, CAT, horse radish peroxidase, alkaline phosphatase and others, commonly used as detectable enzymes, either in an EIA or in an ELISA), and calorimetric labels such as colloidal gold or colored glass or plastic (eg polystyrene, polypropylene, latex, etc) beads. The label may be coupled directly or indirectly to the desired component of the assay according to methods well known in the art. As indicated above, a wide variety of labels may be used, with the choice of label depending on the sensitivity required, ease of conjugation of the compound, stability requirements, available instrumentation, and disposal provisions.

Non-radioactive labels are often attached by indirect means. Generally, a ligand molecule (eg biotin) is covalently bound to the molecule. The ligand then binds to an anti-ligand (eg streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, eg by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, eg luminol.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence, eg by microscopy, visual inspection, via photographic film, by the use of electronic detectors such as charge coupled devices (CCDs) or photomultipliers and the like. Similarly, enzymatic labels are detected by providing appropriate substrates for the enzyme and detecting the resulting reaction product. Finally, simple colorimetric labels may be detected simply by observing the colour associated with the label. Thus, in various dipstick assays, conjugated gold often appears pink, while various conjugated beads appear the colour of the bead.

The ligands of the invention can also be used to detect targets extracted into solution from a solid material. For example, a solid sample can be extracted with an aqueous, an organic solvent or a critical fluid and the resultant supernatant can be contacted with the ligand. Examples of solid samples include animal-derived products, particularly those that have been exposed to agents that transmit prions, eg bone meal derived from bovine sources. Ligands in some embodiments can be used to detect the presence of prion protein in soil. Other solid samples include brain tissue, corneal tissue, faecal matter, bone meal, beef by-products, sheep, sheep by-products, deer and elk, deer and elk by-products, and other animals and animal derived products.

Alternatively, the prion-ligand complexes may be treated with PK. PrPc is highly sensitive to PK, while PrPsc is partially digested to form PrPres. The PrPres molecule itself is highly resistant to proteolysis. Thus, PK treatment will digest PrPc, and will convert PK sensitive PrPsc to PrPres. Following removal of PK, the PrPres can be denatured and detected by antibodies such as 3F4.

In another embodiment, ligands according to the invention may be used for the selective concentration of PrPsc over PrPc.

Use of Ligands to Quantify Prions

A ligand-prion complex, or alternatively, an antibody to the ligand or ligand-prion complex, can be detected and quantified by any of a number of means well known to those of skill in the art. These include analytic biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitation reactions, immunodiffusion (single or double), immunoelectrophoresis, radioimmunoassays (RIAs), enzyme-linked immunosorbent assays (ELISAs), immunofluorescent assays, and the like.

Reduction of Non-Specific Binding

One of skill will appreciate that it is often desirable to reduce non-specific binding in assays and during analyte removal from a sample. Where the assay involves a ligand or other capture agent immobilized on a solid substrate, it is desirable to minimize the amount of non-specific binding to the solid substrate. Means of reducing such non-specific binding are well known to those of skill in the art. Typically, this involves coating the substrate with a proteinaceous composition. In particular, protein compositions such as bovine and human serum albumin (BSA), non-fat powdered milk, and gelatin are widely used.

Other Assay Formats

Western blot analysis can also be used to detect and quantify the presence of prion protein in a sample. The technique generally involves separating sample products by gel electrophoresis on the basis of molecular weight in the presence of SDS, transferring the separated proteins to a suitable solid support (such as a nitrocellulose filter, a nylon filter, or derivatised nylon filter), and incubating the bound sample with the ligands described herein. The ligands specifically bind to a prion peptide fixed on the solid support. These ligands are directly labeled or, alternatively, they may be subsequently detected using labeled antibodies that specifically bind to the ligand.

Other assay formats include liposome immunoassays (LIAs), which use liposomes designed to bind specific molecules (eg ligands) and release encapsulated reagents or markers. The released chemicals are then detected according to standard techniques.

Pharmaceutical Compositions

The ligands described herein that are not coupled to a support matrix are useful in therapeutic and prophylactic applications for the treatment of TSEs caused by infection of a mammal with prion organisms. The ligand may prevent polymerization of PrPsc through inhibition of the binding of PrPsc to PrPsc. In addition it may prevent inhibit binding of PrPsc to PrPc, so decreasing PrPsc mediated conversion of PrPc to PrPsc and thereby delaying the onset of clinical symptoms. Moreover, the ligands themselves may be modified by the addition of a reactive agent to target that molecule to the site of PrPsc accumulation. Such compositions are suitable for use in a variety of drug delivery systems.

Diseases to be treated in accordance with the method include, but are not limited to, BSE, transmissible mink encephalopathy, feline spongiform encephalopathy, CWD, CJD, GSS, fatal insomnia, and vCJD.

The pharmaceutical compositions are intended for parenteral, topical, oral or local administration. Preferably, the pharmaceutical compositions are administered parenterally, eg intravenously, subcutaneously, intradermally, intranasally or intramuscularly. Thus, the invention provides compositions for parenteral administration that comprise a solution of the agents described above dissolved or suspended in an acceptable carrier, preferably an aqueous carrier. A variety of aqueous carriers may be used, eg water, buffered water, 0.4% saline, 0.3% glycine, hyaluronic acid, fibrin sealant and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 1-95% of active ingredient and more preferably at a concentration of 25%-75%.

For aerosol administration, the active ingredients are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, eg lecithin for intranasal delivery.

The amount administered will vary depending upon what is being administered, the state of the mammal receiving treatment and the manner of administration. In therapeutic applications, compositions are administered to a mammal already suffering from prion infection in an amount sufficient to inhibit spread of the prions, or at least partially arrest the symptoms of the disease and its complications. An amount adequate to accomplish this is defined as "therapeutically effective dose." Amounts effective for this use will depend on the severity of the disease, the particular composition, and the weight and general state of the recipient. Generally, the dose will be in the range of about 1 mg to about 5 mg per day, preferably about 100 mg per day, for a 70 kg patient.

Example 1

Identification of Prion-Binding Ligands

The prion-binding ligands described in the Tables below were identified as follows.

Mimetic Library Synthesis

Two 8×8 combinatorial libraries of mimetic ligands on epoxide-activated Purabead 6XL were synthesized (Library A and Library B). PuraBead 6XL is a porous beaded agarose support which is cross-linked to aid durability. The methods of synthesis were similar to those described in WO 97/10887, and could be repeated easily by a practitioner skilled in the art. In summary, after completion of synthesis, each library member comprised a triazine moiety linked to Purabead 6XL by a flexible aminated spacer. The triazine component of each library member was further substituted with two other amines.

Library A

The flexible aminated spacer for this library was three carbon atoms in length, and was introduced by sequential reaction of cross-linked Purabead 6XL with epichlorhydrin and ammonia. Table 1 summarises the further two amines incorporated onto the triazine of each library member, these amines corresponding to the groups —Z—$R^1$ and —Y—$R^2$ of formula (I). The amines are referred to by the following numbers, the ligand identified as 1/1 comprising two 2-adamantamine groups, that identified as 2/1 comprising one 4-(2-aminoethyl)-morpholine group and one 2-adamantamine group, etc:

1=2-Adamantamine
2=4-(2-Aminoethyl)-morpholine
3=1-(2-Aminoethyl)-piperidine
4=1-(2-Aminoethyl)-piperazine
5=(+/−)-2-Aminonorbornane
6=1-(2-Aminopropyl)-2-pyrrolidinone
7=3-Aminoquinuclidine
8=1-(2-Hydroxyethyl)-piperazine
9=N,N-Dimethyl ethylenediamine

TABLE 1

| 1/1 | 2/1 | 3/1 | 5/1 | 6/1 | 7/1 | 8/1 | 9/1 |
|-----|-----|-----|-----|-----|-----|-----|-----|
| 1/2 | 2/2 | 3/2 | 5/2 | 6/2 | 7/2 | 8/2 | 9/2 |
| 1/3 | 2/3 | 3/3 | 5/3 | 6/3 | 7/3 | 8/3 | 9/3 |
| 1/4 | 2/4 | 3/4 | 5/4 | 6/4 | 7/4 | 8/4 | 9/4 |
| 1/5 | 2/5 | 3/5 | 5/5 | 6/5 | 7/5 | 8/5 | 9/5 |
| 1/7 | 2/7 | 3/7 | 5/7 | 6/7 | 7/7 | 8/7 | 9/7 |
| 1/8 | 2/8 | 3/8 | 5/8 | 6/8 | 7/8 | 8/8 | 9/8 |
| 1/9 | 2/9 | 3/9 | 5/9 | 6/9 | 7/9 | 8/9 | 9/9 |

The loading of ligand onto the resin was 12 mmol/g of settled resin, as determined by assay of free amine after addition of the aminated spacer, and assay of chloride release after addition of trichlorotriazine to the aminated spacer.

Library B

The flexible aminated spacer for this library was ten carbon atoms in length, and was introduced by sequential reaction of cross-linked Purabead 6XL with 1,4-butanedioldiglycidyl ether and ammonia. Table 2 summarises the further two amines incorporated onto the triazine of each library member, the amines being referred to by the following numbers:

10=β-Alanine
11=2-Aminoethyl-pyridine
12=3-Aminobenzyl alcohol
13=Phenethylamine
14=Tyramine
15—4-Fluorobenzylamine
16—4-Methylbenzylamine
17—2-(4-Chlorophenyl)-ethylamine
18—Tryptamine
19—Glycine
20—L-Glutamic acid
21—DL-Valine
22—5-Aminovaleric acid
23—4-Aminobutyric acid
24—L-Tyrosine
25—ε-Aminocaproic acid

TABLE 2

| 10/11 | 19/11 | 20/11 | 21/11 | 22/11 | 23/11 | 24/11 | 25/11 |
|-------|-------|-------|-------|-------|-------|-------|-------|
| 10/12 | 19/12 | 20/12 | 21/12 | 22/12 | 23/12 | 24/12 | 25/12 |
| 10/13 | 19/13 | 20/13 | 21/13 | 22/13 | 23/13 | 24/13 | 25/13 |
| 10/14 | 19/14 | 20/14 | 21/14 | 22/14 | 23/14 | 24/14 | 25/14 |
| 10/15 | 19/15 | 20/15 | 21/15 | 22/15 | 23/15 | 24/15 | 25/15 |
| 10/16 | 19/16 | 20/16 | 21/16 | 22/16 | 23/16 | 24/16 | 25/16 |
| 10/17 | 19/17 | 20/17 | 21/17 | 22/17 | 23/17 | 24/17 | 25/17 |
| 10/18 | 19/18 | 20/18 | 21/18 | 22/18 | 23/18 | 24/18 | 25/18 |

The loading of ligand onto the resin was 19 mmol/g of settled resin, as determined by assay of free amine after addition of the aminated spacer, and assay of chloride release after addition of trichlorotriazine to the aminated spacer.

Mimetic Library Binding Screening

The library was inverted several times, allowed to settle and drained by gravity, followed by 2 washes with 1 mL of water and 1 wash with 1 mL 10 mM PBS, pH 7.4 per well. The wells were stopped and 0.5 mL of PBS was added per well. The library was stored overnight under refrigeration. Two tubes containing 1.8 mL of a 10% hamster brain homogenate (HaBH) each were removed from storage in liquid nitrogen and thawed. 180 μL of 5% sarkosyl was added to each tube. The suspension was incubated under tumbling for 30 minutes at room temperature, followed by centrifugation for 10 minutes at 13,400 rpm in a benchtop microcentrifuge. The supernatant was collected, and diluted 1:10 with PBS (final dilution of HaBH: 1:100). The library was drained by gravity, and 500 μL of the HaBH solution added per well, and drained by gravity to a collection plate. Once the wells had drained, each well was washed with an additional 500 μL of PBS, which was collected in the same collection plate. This collection plate was labeled as 'Non-Bound'. 500 μL of 1 M NaCl in PBS was added to each well, and collected in another collection plate labelled 'Salt Elution', followed by 500 μL of 2% acetic acid solution, also collected in a collection plate labelled 'Acetic Acid Elution'. Aliquots of 26 μL of each resin were transferred to microcentrifuge tubes, and stored for analysis of remaining bound prion. The Non-Bound, Salt Elution, and Acetic Acid Elution solutions were frozen in the collection plates.

Dilutions of the HaBH solution at final concentrations of 1:200 and 1:500 were used as controls for SDS-PAGE and western blots.

Western Blot and SDS PAGE Analysis of Non-Bound Fractions

50 μL of each of the 'Non-Bound' samples was added to 50 μL of a 2× Sample Buffer/Reducing Agent (Mixture of Invitrogen NuPAGE LDS Sample Buffer 4× (25 μL), Invitrogen NuPAGE Sample Reducing Agent (10 μL), and ACS grade water (15 μL)). Each tube was heated at 90° C. for 10 minutes.

Duplicate gels were run to allow Western Blot and SDS PAGE analysis of total protein. The format of samples in each 17 well gel was as follows:

| Well | Analyte | Volume (μL) |
|------|---------|-------------|
| 1 | Invitrogen SeeBlue Plus2 Molecular Weight Markers (Cat # LC5925) | 5 |
| 2 | Hamster Brain Homogenat (1:200) | 10 |
| 3 | Hamster Brain Homogenat (1:500) | 10 |
| 4-17 | 14 different 'Non-Bound' samples | 10 |

A 17-well NuPAGE gel cassette was rinsed with deionised water. The white tape strip and comb were removed, lanes rinsed with 1× NuPAGE MES running buffer (Cat # NP0002), and the cassette placed in the gel reservoir of an Xcell Mini-Gel Module (or compatible). The central reservoir was filled with 200 mL of 1× NuPAGE MES running buffer containing 500 μL of NuPAGE antioxidant (Cat # NP0005). After checking for leaks, the outer reservoir was filled with 1× NuPAGE MES running buffer (no added antioxidant). The Mini-Gel Module was attached to a compatible power supply, and the gels run for approximately 45 minutes at a constant 200 V until the dye front was within 0.5 cm of the gel bottom.

SDS Page

The gel was removed from the gel cassette and rinsed three times with ACS water (25 mL, 5 minutes). The gel was stained over one hour with Invitrogen SimplyBlue Safestain, before destaining with three washes with ACS water (25 mL, 1 hour).

Western Blot

A 17-well NuPAGE gel cassette (cat. # NP0349) was rinsed with deionized water and the lanes rinsed with 1× NuPAGE running buffer. The gel was placed in a Xcell Mini-Gel Module (Invitrogen cat #EI0001) or compatible apparatus. The lower chamber was filled with 1× running buffer from stock solution (Invitrogen 20× NuPAGE MES Running Buffer cat #NP0002 or # NP0002-02). The upper chamber was filled with 1× running buffer containing antioxidant (Invitrogen cat #NP0005).

To each sample was added sample buffer containing the reducing agent (Invitrogen cat #NP0007 and cat #NP0004), and the samples heated at 90° C. for 10 minutes, centrifuged briefly, and 5 μL of each sample loaded. 5 μL of the molecular weight marker (Invitrogen cat #LC5925) was also loaded.

The gel was electrophoresed for 45 minutes at a constant 200 V. After the run was complete, the cassette was removed from the unit, opened, and the gel removed. The gel was soaked in chilled transfer buffer for 5 minutes.

The transfer membrane was wetted in methanol, transferred to transfer buffer, and incubated for 2×10 minutes under agitation. Electrode transfer buffer from stock solution (Invitrogen cat #NP0006-1) was prepared with the addition of 20% methanol and antioxidant, and chilled before use. The reservoir of the transfer chamber (BioRad cat #170-4070) was half-filled with chilled electroblot transfer buffer. A BioRad transfer unit cassette in a plastic BioRad transfer cassette tray was made ready with adequate volumes of chilled electroblot transfer buffer. The transfer sandwich was prepared by layering in sequence sponge, filter paper, PVDF transfer membrane (Invitrogen cat. # LC2005), gel, filter paper, and sponge. The cassette was folded and clamped shut. Gels were transferred for 45 minutes at a constant 100V, with the chamber at room temperature.

After transfer, the membrane was placed in a clean dish and incubated for 1 hour, on a rocking platform, at room temperature, in 25 mL of Western Breeze blocking agent from Invitrogen Western Breeze Chemiluminescence Kit, anti-Mouse (cat. # WB7104).

The membrane was then incubated in a 1:10000 dilution of Signet 3F4 primary antibody 3F4 mouse monoclonal antibody (SIGNET, cat #9620) stock solution in 20 mL fresh Western Breeze Primary Antibody Diluent overnight, under refrigeration, on a rocking platform. The blot was rinsed 3 times in 20 mL of Western Breeze Antibody Wash and the membrane then incubated in 1:10,000 KPL-AP secondary antibody (KPL, cat. # 075-1802) in 20 mL Western Breeze Primary Antibody Diluent for 60 mins at room temperature on a rocking platform. The blot was rinsed as above then washed with 20 mL of 20 mM Tris-HCl, 1 mM $MgCl_2$ at pH 9.8 for 10 mins at room temperature. The membrane was transferred to a dry clean dish and soaked with 5 mL Western Breeze pre-mixed Chemiluminescence Substrate (CDP Star) for 5 mins under gentle agitation. The alkaline phosphatase was allowed to react over 30 minutes. The blot was transferred in a sheet protector to a film cassette and exposed to film (Amersham cat. # RPN-3130K) for 5 min at room temperature and develop in a developer.

Example 2

Use of ligand 5/4 Attached to Agarose for Capture of PrPc From Red Blood Cell Concentrate An adsorbent comprising ligand 5/4 attached to Purabead 6XL base matrix was synthesised as described in Example 1 to provide a compound of formula (VI):

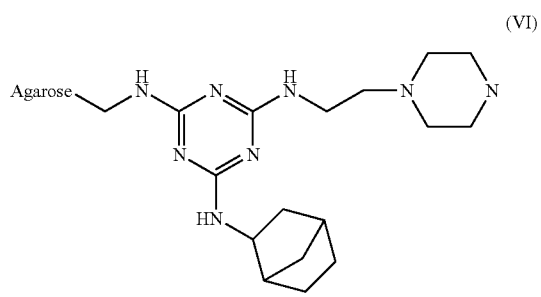

(VI)

A sample of 10% w/v normal hamster brain homogenate in PBS buffer (100 µl) was thawed and 10 µl of 10% (w/v) sarcosyl added, vortex mixed and stored in wet ice for 30 minutes. The mixture was centrifuged at 14,000 rpm for 5 minutes at +4° C. and the supernatant removed. Human red blood cell concentrate (RBCC; 250 ml) was mixed with Adsol (110 ml) and gently mixed by inversion. Diluted RBCC (1.8 ml) was removed and mixed with 0.2 ml hamster brain homogenate solution.

A 1:1 suspension (400 µl) of compound (VI) suspended in 40 mM Citrate buffer/280 mM NaCl pH 7.0, was added to a 1.0 ml micro-column and allowed to drain under gravity. Hamster Brain homogenate in RBCC (1 ml) was pipetted onto the settled affinity adsorbent and allowed to drain. The adsorbent was subsequently washed with 1 ml of suspension buffer and allowed to drain. Both flow through fractions were collected, combined and stored at −20° C.

The affinity adsorbent was removed from the column by suspending in 0.5 ml of suspension buffer and transferred to a cryovial. The volume of affinity adsorbent transferred was recorded after allowing the vial contents to settle and the volume of supernatant adjusted to provide a 1:1 slurry. A sample (200 µl) was transferred to a microfuge vial for use in SDS-PAGE and Western blot analysis of bound prion as described in Example 1.

The presence of strong bands by western blot corresponding to hamster PrPc indicated ligand 5/4 attached to Purabead 6XL (beaded agarose matrix) was able to bind PrPc selectively from human red cell concentrate.

Example 3

Preparation of Prion Binding Ligands Attached to Polymethacrylate Resin Beads

This example describes the preparation of a number of ligands containing amines used in Libraries A and B, but on aminated polymethacrylate supports (Toyopearl 650M), rather than agarose.

3.1 Dichlorotriazine Derivative of Aminated Toyopearl 650M

Toyopearl AF—Amino-650M (36 g) was washed on a sinter funnel with ten portions (36 mL) of RO-water, then the gel drained and re-suspended in 1 M potassium phosphate pH 7.0 (36 mL). The gel was allowed to drain and then re-suspended in 1 M potassium phosphate pH 7.0 (27 mL) and RO-water (27 mL). This mixture was transferred to a stirred glass reaction vessel and 54 mL of acetone added. The mixture was cooled to 0° C., then to this was added cyanuric chloride (2.7 g) dissolved in cold (0° C.) acetone (27 mL) and the mixture stirred for 1 h at 0-4° C. The resulting slurry of dichlorotriazine activated product was poured onto a glass sinter and washed with aqueous acetone (50% v/v, 180 mL), RO-water (180 mL), aqueous acetone (50% v/v, 180 mL) and RO-water (360 mL).

3.2 Monochlorotriazine Intermediates

Various monochlorotriazine intermediates were prepared from the dichlorotriazine-activated Toyopearl 650M as follows:

3.2.1 The monochlorotriazine aminated Toyopearl 650M adduct of 1-(2-aminoethyl)piperidine (amine 3) was prepared by dissolving 1-(2-aminoethyl)piperidine (0.47 g) in RO-water (28.8 mL) and cooling the solution to 4° C. This mixture was added to 7 g of dichlorotriazine-activated aminated Toyopearl that had been drained in water on a glass sinter, transferred to a plastic reaction vessel and cooled to 4° C. The mixture was shaken at 4° C. for 2 h, then the mixture was poured into a glass sinter, washed with aqueous DMF (50% v/v, 35 mL), RO-water (70 mL), then allowed to drain on the sinter.

3.2.2 The monochlorotriazine aminated Toyopearl 650M adduct of (+/−) 2-aminonorbornane (amine 5) was prepared by dissolving (+/−) 2-aminonorbornane (0.82 g) in aqueous DMF (13.3% v/v, 57.68 mL), and cooling the solution to 4° C.

This mixture was added to 14 g of dichlorotriazine-activated aminated Toyopearl that had been drained in water on a glass sinter, transferred to a plastic reaction vessel and cooled to 4° C. The mixture was shaken for 2 h at 4° C., then the mixture poured into a glass sinter and washed with aqueous DMF (50% v/v, 70 mL), RO-water (140 mL), then allowed to drain on the sinter.

3.2.3 The monochlorotriazine aminated Toyopearl 650M adduct of L-glutamic acid (amine 20) was prepared by dissolving L-glutamic acid (0.515 g) in aqueous DMF (50% v/v, 28.0 mL) and aqueous sodium hydroxide (10 M, 0.7 mL) then cooling the solution to 4° C. This mixture was added to dichlorotriazine-activated aminated Toyopearl (7 g) that had been drained in water on a glass sinter, transferred to a plastic reaction vessel and cooled to 4° C. The mixture was shaken for 70 min at 4° C., then the mixture poured into a glass sinter and washed with aqueous DMF (50% v/v, 70 mL), RO-water (140 mL), then allowed to drain on the sinter.

3.2.4 The monochlorotriazine aminated Toyopearl 650M adduct of 5-aminovaleric acid (amine 22) was prepared by dissolving 5-aminovaleric acid (0.41 g) in aqueous DMF (50% v/v, 28.5 mL) and aqueous sodium hydroxide (10 M, 0.35 mL) and cooling the solution to 4° C. This mixture was added to 7 g of dichlorotriazine-activated aminated Toyopearl that had been drained in water on a glass sinter, transferred to a plastic reaction vessel and cooled to 4° C. The mixture was shaken for 60 min at 4° C., then the mixture poured into a glass sinter and washed with aqueous DMF (50% v/v, 70 mL), RO-water (140 mL), then allowed to drain on the sinter.

3.2.5 The monochlorotriazine aminated Toyopearl 650M adduct of glycine (amine 19) was prepared by dissolving glycine (0.563 g) in aqueous DMF (50% v/v, 61.4 mL) and aqueous sodium hydroxide (10 M, 0.75 mL) and cooling the solution to 4° C. This mixture was added to 15 g of dichlorotriazine-activated aminated Toyopearl that had been drained in water on a glass sinter, transferred to a plastic reaction vessel and cooled to 4° C. The mixture was shaken for 60 min at 4° C., then the mixture poured into a glass sinter and washed with aqueous DMF (50% v/v, 75 mL), RO-water (150 mL), then allowed to drain on the sinter.

3.3 Final Products

Solutions of amines for the second stage reactions were prepared as follows:

3.3.1 1-(2-Aminoethyl)piperidine (amine 3; 0.94 g) was dissolved in RO-water (10.8 mL).
3.3.2 1-(2-Aminoethyl)piperazine (amine 4; 1.90 g) was dissolved in RO-water (21.6 mL), then split into two portions (11.8 mL each).
3.3.3 2-(2-Aminoethyl)pyridine (amine 11; 0.84 mL) was dissolved in aqueous DMF (50% v/v, 10.9 mL).
3.3.4 Phenylethylamine (amine 13; 0.88 mL) was dissolved in aqueous DMF (50% v/v, 10.9 mL), made up in two equal portions.
3.3.5 Tyramine (amine 4; 0.96 g) was dissolved in DMF (10.8 mL).

Reaction mixtures were assembled from combinations of the appropriate monochlorotriazine intermediate and second-stage amine, made up in plastic reaction vessels containing the monochlorotriazine intermediate (7 g) and the amine solution to a total solvent volume of 35 mL, including 5.75 ml RO-water within the 7 g of monochlorotriazine intermediate. Each vessel was tumbled at 60° C. for 24 h. The gels were then washed with aqueous DMF (50% v/v, 35 mL), RO-water (35 mL), 0.1 M hydrochloric acid (35 ml), aqueous isopropanol (30% v/v) containing sodium hydroxide (0.2 M) (35 ml), RO-water (70 mL) and aqueous ethanol (20% v/v, 21 mL) and stored in aqueous ethanol (20% v/v) at 4° C.

Example 4

Use of Prion Binding Ligands Attached to Polymethacrylate Resin for Capture of PrPsc from Red Blood Cell Concentrate Compounds comprising affinity ligands attached to a beaded polymethacrylate matrix (Toyopearl) were synthesised as described in Example 3. An extract (1% w/v) of scrapie infected hamster brain spiked into human red blood cell concentrate (RBCC) was prepared using the procedure described for normal hamster brain homogenate (Example 2). The binding of PrPsc by the polymethacrylate affinity adsorbents was assessed by packing adsorbent slurries in 1 ml microcolumns and challenging with spiked RBCC using the procedure described in Example 2. SDS-PAGE and western blots of samples extracted from the affinity adsorbents was performed as described in Example 1 with the exception that a second set of sample aliquots were treated with proteinase K before mixing with SDS-PAGE reducing buffer.

Western blot analysis indicated that polymethacrylate resins containing ligands 5/4, 19/13, 5/3, 22/13 and 19/14 |all demonstrated high affinity for PrPsc in the presence of human red blood cell concentrate. The binding of PrPsc was confirmed by comparison of the western blot banding pattern obtained +/− proteinase K treatment. The presence of clearly visible bands of slightly lower molecular weight for the proteinase K treated sample compared to the non-treated sample confirmed binding of the proteinase K resistant form (infectious form) of PrP.

Example 5

Use of Prion Binding Ligands Attached to Polymethacrylate Resin for Capture of the Human Sporadic CJD Causitive Prion from Red Blood Cell Concentrate The experiment described in Example 4 was repeated using RBCC spiked with 1% (w/v) human sporadic CJD brain homogenate. Western blot analysis indicated that polymethacrylate resins containing ligands 5/4, 19/13, 5/3, 22/13 and 3/4 |all demonstrated high affinity for PrP from human sporadic CJD brain in the presence of human red blood cell concentrate.

Example 6

Use of ligand 5/4 Attached to Polymethacrylate Resin Beads for Capture of PrPsc from Human Plasma and Human Blood An affinity adsorbent comprising ligand 5/4 attached to a beaded polymethacrylate matrix (Toyopearl) was synthesised as described in Example 3. Extracts (1% w/v) of scrapie infected hamster brain spiked into human pooled plasma and human whole blood were prepared using the procedure described for normal hamster brain homogenate and RBCC (Example 2). The binding of PrPsc by the polymethacrylate affinity adsorbents was assessed by packing adsorbent slurries in 1 ml microcolumns and challenging with spiked plasma and whole blood samples using the procedure described in Example 2. SDS-PAGE and western blots of samples extracted from the affinity adsorbents was performed as described in Example 1 with the exception that a second set of sample aliquots were treated with proteinase K before mixing with SDS-PAGE reducing buffer.

Western blot analysis indicated that polymethacrylate resins containing ligands 5/4 demonstrated high affinity for PrPsc in the presence of human plasma and whole human blood. The binding of PrPsc was confirmed by comparison of the western blot banding pattern obtained +/− proteinase K treatment. The presence of clearly visible bands of slightly lower molecular weight for the proteinase K treated sample compared to the non-treated sample confirmed binding of the proteinase K resistant form (infectious form) of PrP.

It will be apparent to one skilled in the art that ligand 5/4 and other ligands described herein attached to a support matrix such as polymethacrylate are especially useful for the capture and concentration of a wide variety of prion protein forms from various blood components, including whole blood, RBCC and plasma. Such materials are therefore of exceptional value for the removal of PrP from such components and as a means of PrP concentration to aid subsequent detection and quantitation.

Although methods and materials similar or equivalent to those described herein can be used in the practice or testing of the present invention, suitable methods and material are described above. All publications, patent applications, patents and other cited references mentioned herein are incorporated by reference in their entirety. In addition, the materials, methods, and examples are illustrative only and not intended to be limiting.

The foregoing description is provided for describing various embodiments relating to the invention. Various modifications, additions and deletions may be made to these embodiments and/or structures without departing from the scope and spirit of the invention.

Z represents an oxygen atom, a sulfur atom or $NR^4$;

Y represents an oxygen atom, a sulfur atom or $NR^5$;

wherein $R^4$ and $R^5$, which may be the same or different, represent hydrogen, optionally substituted alkyl containing 1 to 6 carbon atoms, optionally substituted phenyl, optionally substituted benzyl or optionally substituted β-phenylethyl; and $X^1$ and $X^2$ both represent a nitrogen atom;

$R^1$ represents a group $—(CH_2)_m-Q^1$, wherein m is from 0 to 7, and $Q^1$ represents $—NR^{11}R^{12}$, in which $R^{11}$ and $R^{12}$, together with the nitrogen atom to which they are attached, form an optionally substituted heterocycloalkyl group, and $R^2$ represents a group $—(CH_2)_n-Q^2$, wherein n is from 0 to 7, and $Q^2$ represents $—CR^{21}R^{22}R^{23}$ or $—NR^{21}R^{22}$, in which $R^{23}$ represents hydrogen, alkyl, cycloalkyl or heterocyclo-alkyl, and $R^{21}$ and $R^{22}$, together with the carbon or nitrogen atom to which they are attached, form an optionally substituted cycloalkyl or optionally substituted heterocycloalkyl group;

wherein the compound has affinity for binding the prion protein.

The invention claimed is:

1. A method for detecting a prion protein in a sample, and/or removing a prion protein from a sample, which method comprises contacting the sample with a compound of formula (I)

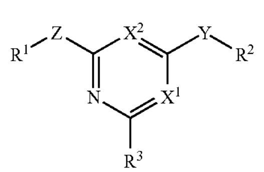

(I)

wherein $R^3$ is hydrogen or an aryl group substituent or $R^3$ is a solid support optionally attached via a spacer;

2. A compound of formula (I)

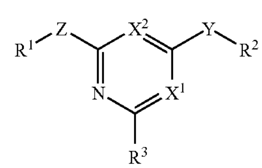

(I)

wherein $R^3$ is hydrogen or an aryl group or $R^3$ is a solid support optionally attached via a spacer;

Z represents NH;

Y represents NH;

$X^1$ and $X^2$ both represent a nitrogen atom;
$R^1$ represents a group $-(CH_2)_m-Q^1$, wherein m is 2, and $Q^1$ represents
piperidyl or piperazinyl, and
$R^2$ represents a group $-(CH_2)_n-Q^2$, wherein n is 0 or 2, and $Q^2$ represents 1-piperidyl or adamantyl.

3. A pharmaceutical composition comprising:
a compound according to claim 2, wherein $R^3$ is hydrogen or an aryl group substituent; and
a pharmaceutically acceptable carrier.

* * * * *

```
                          SEQUENCE LISTING

<160> NUMBER OF SEQ ID NOS: 1

<210> SEQ ID NO 1
<211> LENGTH: 8
<212> TYPE: PRT
<213> ORGANISM: artificial
<220> FEATURE:
<223> OTHER INFORMATION: octapeptide repeat sequence of mammalian prion
      proteins

<400> SEQUENCE: 1

Pro His Gly Gly Gly Trp Gly Gln
1               5
```